(12) United States Patent
Nassif (10) Patent No.: US 7,962,207 B2
(45) Date of Patent: Jun. 14, 2011

(54) METHOD AND APPARATUS FOR VARIABLE CAPACITANCE DEFIBRILLATION

(75) Inventor: Rabih C. Nassif, Corona, CA (US)

(73) Assignee: Cardiac Science Corporation, Bothell, WA (US)

( * ) Notice: Subject to any disclaimer, the term of this patent is extended or adjusted under 35 U.S.C. 154(b) by 191 days.

(21) Appl. No.: 12/274,967

(22) Filed: Nov. 20, 2008

(65) Prior Publication Data

US 2009/0076558 A1  Mar. 19, 2009

Related U.S. Application Data (63) Continuation of application No. 11/223,782, filed on Sep. 9, 2005, now Pat. No. 7,457,662.

(51) Int. Cl.
*A61N 1/39* (2006.01)

(52) U.S. Cl. .................. 607/5; 607/4

(58) Field of Classification Search .................. None
See application file for complete search history.

(56) References Cited

U.S. PATENT DOCUMENTS

| | | | |
|---|---|---|---|
| 2,943,628 A | 7/1960 | Howell | |
| 3,211,154 A | 10/1965 | Becker et al. | |
| 3,886,950 A | 6/1975 | Ukkestad et al. | |
| 4,077,413 A * | 3/1978 | Partridge | 607/5 |
| 4,165,749 A | 8/1979 | Cansell | |
| 4,328,808 A | 5/1982 | Charbonnier et al. | |
| 4,574,810 A | 3/1986 | Lerman | |
| 4,619,265 A | 10/1986 | Morgan et al. | |
| 4,768,512 A | 9/1988 | Imran | |
| 4,785,812 A | 11/1988 | Pihl et al. | |
| 4,840,177 A | 6/1989 | Charbonnier et al. | |
| 4,850,356 A | 7/1989 | Heath | |
| 5,111,813 A | 5/1992 | Charbonnier et al. | |
| 5,199,429 A | 4/1993 | Kroll et al. | |
| 5,215,081 A | 6/1993 | Ostroff | |
| 5,342,400 A | 8/1994 | Hirschberg et al. | |
| 5,385,575 A | 1/1995 | Adams | |

(Continued)

FOREIGN PATENT DOCUMENTS

EP  0128103 A1  5/1984

(Continued)

OTHER PUBLICATIONS

Michael R. Gold, M.D., PhD., *Biphasic Defibrillation: Increasing Efficacy While Decreasing Risk*, 4 Pgs., Copyright 2002.

(Continued)

*Primary Examiner* — Carl H. Layno
*Assistant Examiner* — Jon-Eric C. Morales
(74) *Attorney, Agent, or Firm* — Patterson Thuente Christensen Pedersen, P.A.

(57) ABSTRACT

An Automated External Defibrillator (AED) for delivering therapeutic electrical energy to a patient's heart comprising at least one variable capacitance capacitor having a large positive voltage coefficient such that a given amount of energy can be stored at a lower voltage than a traditional fixed capacitor having an equivalent capacitance. Due to the variable capacitance capacitor's ability to store energy at a lower voltage, initial defibrillation current levels are reduced effectively minimizing the risk of tissue damage caused by high initial current levels. In addition, the use of a variable capacitance capacitor reduces the amount of current decay throughout the discharge cycle as opposed to current AED designs utilizing fixed capacitance capacitors which experience an exponential decline in defibrillation current during the discharge cycle.

18 Claims, 5 Drawing Sheets

U.S. PATENT DOCUMENTS

| | | | | |
|---|---|---|---|---|
| 5,391,186 | A | 2/1995 | Kroll et al. | |
| 5,405,361 | A | 4/1995 | Persson | |
| 5,405,363 | A | 4/1995 | Kroll et al. | |
| 5,411,526 | A | 5/1995 | Kroll et al. | |
| 5,413,591 | A | 5/1995 | Knoll | |
| 5,431,686 | A | 7/1995 | Kroll et al. | |
| 5,468,254 | A | 11/1995 | Hahn et al. | |
| 5,507,778 | A | 4/1996 | Freeman | |
| 5,507,781 | A | 4/1996 | Kroll et al. | |
| 5,514,160 | A | 5/1996 | Kroll et al. | |
| 5,531,764 | A | 7/1996 | Adams et al. | |
| 5,534,015 | A * | 7/1996 | Kroll et al. | 607/7 |
| 5,540,723 | A | 7/1996 | Ideker et al. | |
| 5,540,724 | A | 7/1996 | Cox | |
| D372,977 | S | 8/1996 | Bishay | |
| 5,549,112 | A | 8/1996 | Cockburn et al. | |
| 5,591,209 | A | 1/1997 | Kroll et al. | |
| 5,591,211 | A | 1/1997 | Meltzer | |
| 5,593,427 | A | 1/1997 | Gliner et al. | |
| 5,601,612 | A | 2/1997 | Gliner et al. | |
| 5,607,454 | A * | 3/1997 | Cameron et al. | 607/5 |
| 5,643,324 | A | 7/1997 | Persson | |
| 5,716,381 | A | 2/1998 | Reggiardo | |
| 5,733,309 | A | 3/1998 | Kroll et al. | |
| 5,733,310 | A | 3/1998 | Lopin et al. | |
| 5,735,879 | A | 4/1998 | Gliner et al. | |
| 5,741,306 | A | 4/1998 | Glegyak et al. | |
| 5,749,904 | A | 5/1998 | Gliner et al. | |
| 5,766,226 | A | 6/1998 | Pedersen | |
| 5,836,972 | A | 11/1998 | Stendahl et al. | |
| 5,891,173 | A | 4/1999 | Brewer | |
| 5,899,924 | A | 5/1999 | Brewer et al. | |
| 5,913,877 | A | 6/1999 | Kroll et al. | |
| 5,991,658 | A * | 11/1999 | Brewer et al. | 607/7 |
| 6,047,212 | A | 4/2000 | Gliner et al. | |
| 6,119,039 | A * | 9/2000 | Leyde | 607/5 |
| 6,148,233 | A | 11/2000 | Owen et al. | |
| 6,198,967 | B1 | 3/2001 | Brewer et al. | |
| 6,241,751 | B1 | 6/2001 | Morgan et al. | |
| 6,289,243 | B1 | 9/2001 | Lin et al. | |
| 6,374,137 | B1 | 4/2002 | Morgan et al. | |
| 6,374,138 | B1 | 4/2002 | Owen et al. | |
| 6,418,342 | B1 | 7/2002 | Owen et al. | |
| 6,427,083 | B1 | 7/2002 | Owen et al. | |
| 6,546,285 | B1 | 4/2003 | Owen et al. | |
| 7,457,662 | B2 | 11/2008 | Nassif | |
| 7,555,339 | B2 | 6/2009 | Nielsen et al. | |
| 2003/0055460 | A1 | 3/2003 | Owen et al. | |
| 2003/0125771 | A1* | 7/2003 | Garrett | 607/5 |
| 2003/0167075 | A1 | 9/2003 | Fincke | |
| 2009/0237862 | A1 | 9/2009 | Nielsen et al. | |

FOREIGN PATENT DOCUMENTS

| | | |
|---|---|---|
| EP | 0255241 A2 | 6/1987 |
| EP | 0281219 A1 | 1/1988 |
| EP | 0339471 A2 | 4/1989 |
| EP | 0445800 A1 | 3/1991 |
| EP | 0437104 A2 | 7/1991 |
| EP | 0590318 A1 | 4/1994 |
| GB | 2153084 A | 8/1985 |
| WO | WO 90/08466 | 8/1990 |
| WO | WO 93/01861 | 2/1993 |
| WO | WO 93/16759 | 9/1993 |
| WO | WO 94/21327 | 9/1994 |
| WO | WO 94/27674 A1 | 12/1994 |
| WO | WO 95/05215 | 2/1995 |
| WO | WO 95/09673 | 4/1995 |
| WO | WO 95/32020 | 11/1995 |
| WO | WO 95/34344 A1 | 12/1995 |
| WO | WO 97/37719 A1 | 10/1997 |
| WO | WO 98/39061 A3 | 1/1999 |

OTHER PUBLICATIONS

*Morgan v. Owen*, Interference No. 105451, Declaration of Thomas D. Lyster (In support of Morgan Priority Motion before the Board of Patent Appeals), 14 Pgs. Dated May 24, 2007.

Bradford E. Gliner et al., *Transthoracic Defibrillation of Swine with Monophasic and Biphasic Waveforms, Biphasic Transthoracic Defibrillation*, Dated Sep. 15, 1995, pp. 1634-1643.

Bradford E. Gliner, *Comparison of Monophasic and Biphasic Waveform Transthoracic Defibrillation of Swine*, American College of Cardiology 44th Annual Scientific Session Abstract Form, Sep. 9, 1994, Seattle, Washington.

Bradford E. Gliner, *Biphasic Waveform Transthoracic Defibrillation of Swine: Dependence on Waveform Duration, Tilt and Phasic Duration*, American College of Cardiology 44th Annual Scientific Session Abstract Form, Sep. 9, 1994, Seattle Washington.

Application and File History for U.S. Patent 7457662, U.S. Appl. No. 11/223,782, filed Sep. 9, 2005, Inventor Rabih C. Nassif, www.uspto.gov.

Application and File History for U.S. Patent 5891173, Ser. No. 837224, Filed Apr. 10, 1997, Inventor James E. Brewer, www.uspto.gov. Parts 1 and 2.

Application and File History for U.S. Patent 5899924, U.S. Appl. No. 08/833,935, filed Apr. 10, 1997, Inventors James E. Brewer and Gary B. Stendahl, www.uspto.gov.

Application and File History of U.S. Patent Application, U.S. Appl. No. 10/159,806, filed May 31, 2002, Inventors James P. O'Leary and Mark H. Totman, www.uspto.gov.

Pacing and Clinical Electrophysiology, Futura Publishing Co., vol. 19, No. 8 *A Conceptual Basis foir Defibrillation Waveforms*, Brian G. Cleland, pp. 1186-1195, Aug. 1996.

Pacing and Clinical Electrophysiology, Futura Publishing Co., vol. 17, No. 11, Part I, pp. 1782-1792, Nov. 1994.

The Journal of General Physiology, Rockefeller Institute for Medical Research, vol. 15, pp. 708-729, 1932.

Journal of the American College of Cardiology, vol. 13, No. 1, Jan. 1989, pp. 207-214.

Pacing and Clinical Electrophysiology, Futura Publishing Co., vol. 16, No. 4, Part I, pp. 769-777, Apr. 1993.

Circulation, American Heart Association, vol. 82, No. 6, pp. 2128-2141, Dec. 1990.

Circulation, American Heart Association, vol. 76, No. 5, pp. 1176-1184, Nov. 1987.

Circulation, American Heart Association, vol. 91, No. 6, pp. 1768-1774, Mar. 1995.

Circulation, American Heart Association, vol. 92, No. 6, pp. 1634-1643, Sep. 1995.

Circulation, American Heart Association, vol. 94, No. 10, pp. 2507-2514, Nov. 1996.

Basic Electronics, Part 2 Elements of Electricity, www.sweethaven.com, Dated Nov. 7, 2001.

U.S. Appl. No. 10/159,806, Record of Fed. Cir. Appeal., Docket Listing, U.S. Court of Appeals for the Fed. Circuit, *Kloninklijke v. Cardiac Science 2009-1040*, First Captioned Item Oct. 27, 2008.

U.S. Appl. No. 10/159,806, Record of Fed. Cir. Appeal., Selected Documents, U.S. Court of Appeals for the Federal Circuit, *Kloninklijke v. Cardiac Science 2009-1041*, First Captioned Item Mar. 5, 2009. Parts 1, 2, 3, and 4.

U.S. Appl. No. 10/159,806, Record of District Court Proceedings, Selected Documents, U.S. Dist. Ct. for the Western District of Washington (Seattle), Originally Filed on Apr. 8, 2008. Parts 1 and 2.

U.S. Appl. No. 10/159,806, Record of Interference Proceedings Before BPAI, Interference No. 105451, Notice to Declare Interference Filed May 22, 2006. Parts 1, 2, and 3.

McDaniel et al., External Defibrillation with a five element cluster electrode, Abstract, 1999.

Tacker, Jr., W.A., Defibrillation of the Heart ICDs, AEDs, and Manual, p. 197-222, © 1994.

Sweeny, Robert J. et al., An In-Vitro Model of Electrical Defibrillation, Abstract, JACC vol. 21, No. 2, Feb. 1993:307A.

The Journal of General Physiology, Rockefeller Institute for Medical Research, vol. 15, pp. 731-755, 1932.

Pacing and Clinical Electrophysiology, Futura Publishing Co., vol. 18, No. 4, pp. 673-688, Apr. 1995.

Journal of Cardiovascular Electrophysiology, Futura Publishing Co., vol. 6, No. 9, pp. 737-750, Sep. 1995.

Pacing and Clinical Electrophysiology, Futura Publishing Co., vol. 18, No. 3, Part II, pp. 526-538, Mar. 1995.

Brewer et al., Article Entitled "Low Voltage Shocks Have a Significantly Higher Tilt of the Internal Electric Field Than Do High Voltage Shocks", *Pacing and Clinical Electrophysiology*, vol. 18, No. 1, Jan. 1995.

Bradley J. Roth, Article Entitled "Mechanisms for Electrical Stimulation of Excitable Tissue", *Critical Reviews in Biomedical Engineering*, vol. 22/Issues 3 & 4/1994.

Wikswo, Jr. et al., Article Entitled "Virtual Electrodes in Cardiac Tissue: A Common Mechanism for Anodal and Cathodal Stimulation", *Biophysical Journal*, vol. 69, No. 6, Dec. 1995.

Bradley J. Roth, Article Entitled "A Mathematical Model of Make and Break Electrical Stimulation of Cardiac Tissue by a Unipolar Anode or Cathode", *IEEE Transactions on Biomedical Engineering, A Publication of the IEEE Engineering in Medicine and Biology Society*, Dec. 1995, vol. 42, No. 12.

Roth et al., Article Entitled "The Effect of Externally Applied Electrical Fields on Myocardial Tissue", *Proceedings of the IEEE*, Mar. 1996, vol. 84, No. 3.

Siegfried S. Meyers, Ph.D., Article Entitled "Impedance-compensated defibrillator", published in the *American Heart Journal*, Sep. 1962, vol. 64, No. 3.

\* cited by examiner

METHOD AND APPARATUS FOR VARIABLE CAPACITANCE DEFIBRILLATION

RELATED APPLICATIONS

This application is a continuation of U.S. application Ser. No. 11/223,782, filed Sep. 9, 2005 now U.S. Pat. No. 7,457,662. The entire disclosure of this related application is expressly incorporated herein by reference.

BACKGROUND OF THE INVENTION

1. Field of the Invention

The present invention is directed to methods and apparatus for defibrillation of a patient's cardiac cell membrane. More specifically, the methods and apparatus of the present invention are directed to the delivery of shocking defibrillation waveforms using at least one variable capacitance capacitor having a large positive voltage coefficient such that energy can be stored at a lower voltage as compared to a traditional fixed capacitance capacitor with an equivalent capacitance.

2. Description of the Related Art

Cardiac arrhythmias, such as ventricular fibrillation and ventricular tachycardia, are electrical malfunctions of the heart, in which regular electrical impulses in the heart are replaced by irregular, rapid impulses. These irregular, rapid impulses can cause the heart to stop normal contractions, thereby interrupting blood flow therethrough. Such an interruption in blood flow can cause organ damage or even death.

Normal heart contractions, and thus normal blood flow, can be restored to a patient through application of electric shock. This procedure, which is called defibrillation, has proven highly effective at treating patients with cardiac arrhythmias, provided that it is administered within minutes of the arrhythmia. To deliver this electric shock, defibrillators, either implantable or portable, have been developed with the intent of quickly delivering life saving treatment.

Portable automatic external defibrillators (hereinafter "AEDs") are often used in facilities drawing large crowds of people such as shopping malls, sporting arenas, office buildings and the like. An AED is typically used by trained emergency medical system personnel, though AEDs typically include step-by-step instructions combined with various sensors that make them usable by almost anyone in an emergency situation.

A typical AED comprises various electrical and electronic components including a controller, a battery circuit, a detector circuit and a discharge circuit. Generally, the discharge circuit includes at least one capacitor for storing energy from the battery circuit and subsequently discharging that energy in the form of defibrillation waveform when requested by the controller. Unfortunately, the capacitors traditionally used in AED's may discharge at initial current levels sufficient enough to cause tissue damage. Furthermore, these traditional capacitors suffer a exponentially steep decline in the level of the defibrillation current as the capacitor discharges.

SUMMARY OF THE INVENTION

The present invention addresses the aforementioned drawbacks associated with the capacitor technology presently utilized in AED's. For example, according to one aspect, the present invention includes at least one variable capacitance capacitor having a large positive voltage coefficient, i.e., a capacitor whose capacitance drastically increases with the amount of charge it contains. The at least one variable capacitance capacitor can store a given amount of energy at a much lower voltage than traditional fixed capacitors having equivalent capacitance ratings. As such, the AED of the present invention allows for a much lower initial current during defibrillation to reduce the risk of tissue damage. Furthermore, the AED of the present invention is better able to maintain the current level of the defibrillation charge throughout the AED discharge sequence. Finally, the lower initial current allows the use of electrical components having lower ratings and capacities to reduce assembly and manufacturing costs.

DETAILED DESCRIPTION OF THE PREFERRED EMBODIMENTS

Figure 1A:
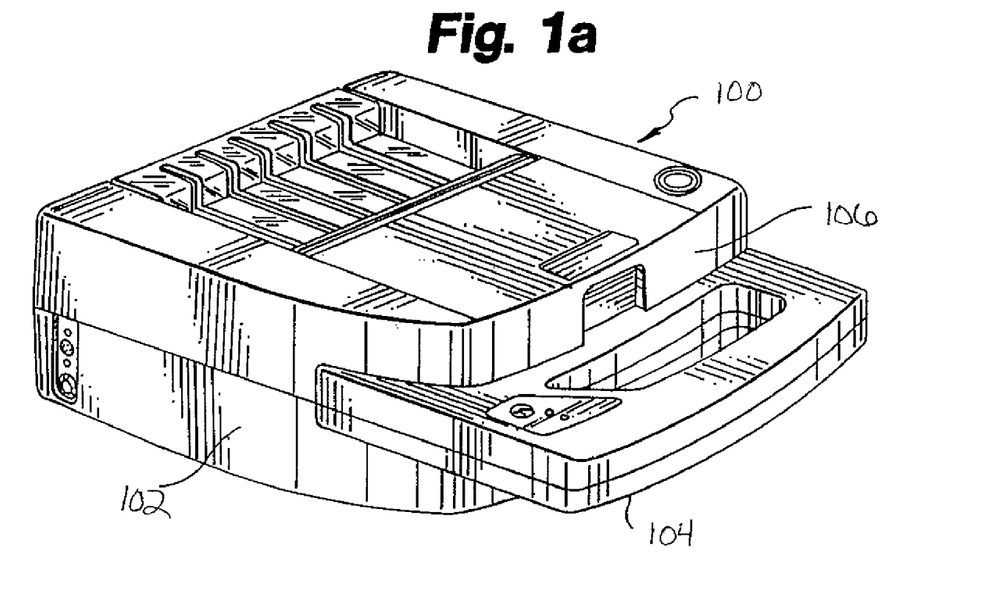
FIG. 1a is a perspective view of an automated external defibrillator in a storage disposition.
Figure 1B:
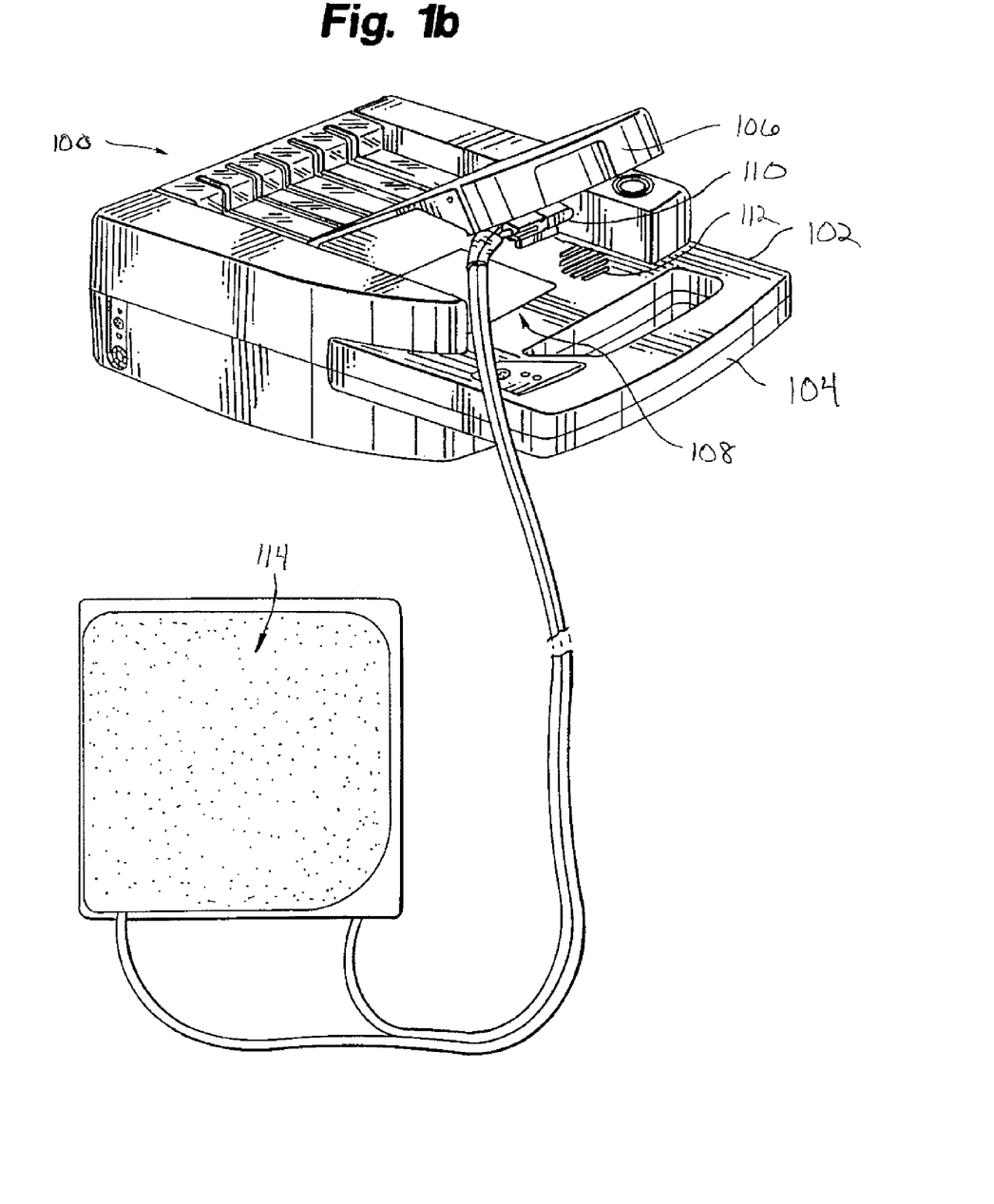
FIG. 1b is a perspective view of the automated external defibrillator of FIG. 1 in an operable disposition.

The present invention is directed to a defibrillation system for use in treating patients who have suffered from cardiac arrhythmias. As depicted in FIG. 1a, an automated external defibrillator (AED) 100 comprises a plastic case 102 having a carrying handle 104. As is more clearly illustrated in FIG. 1b, plastic case 102 further comprises a lid 106 selectively covering an electrode compartment 108. Electrode component 108 comprises an electrode connector 110, a speaker 112 and a diagnostic panel (not shown). A pair of electrodes 114 adapted for attachment to a patient are connected to electrode connector 110. Electrodes 114 are typically stored within electrode compartment 108 and may be preconnected to electrode connector 110 during storage of the AED 100.

The operation of AED 100 is described briefly below. A rescue mode of AED 100 is initiated when lid 106 is opened to access electrodes 114 as depicted in FIG. 2. The opening of lid 106 is detected by AED 100 to effectively turn on the device. Once turned on, AED 100 performs a short test routine. A user applies electrodes 114 to the patient such that AED 100 can measure patient specific parameters, such as impedance, voltage, current, charge or other measurable parameters of the patient. The patient specific parameters are then utilized to design and administer optimal waveform, either monophasic or biphasic, as described below.

If the AED 100 detects a shockable condition, the AED initiates the charging of a plurality of self-contained capacitors using a self-contained energy source, typically a detachable battery pack. The AED 100 then uses the patient specific parameters to calculate an optimal waveform for discharge to the patient. The energy stored within the plurality of capacitors is then discharged through the electrodes 114 to defibrillate the heart. For more detail with respect to the physical structure of AED 100 or the process of AED testing, sensing patient specific parameters, determining shockable conditions, charging capacitors and discharging waveforms, reference is made to Applicant's issued U.S. Pat. No. 5,645,571, which is commonly assigned to the assignee of the present invention and is hereby incorporated by reference in its entirety.

Figure 2A:
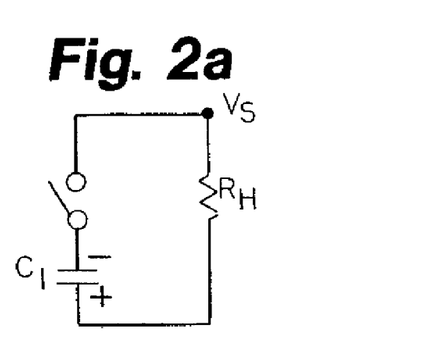
FIG. 2a depicts a basic defibrillation circuit.
Figure 2B:
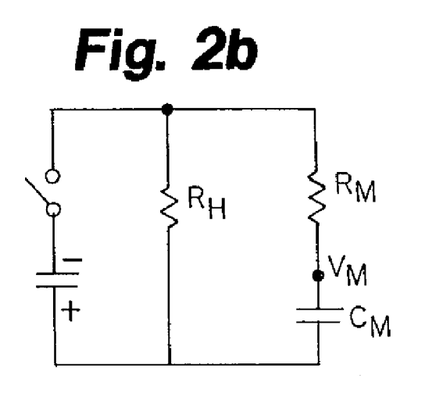
FIG. 2b depicts a basic defibrillation circuit for generating a monophasic waveform.
Figure 2C:
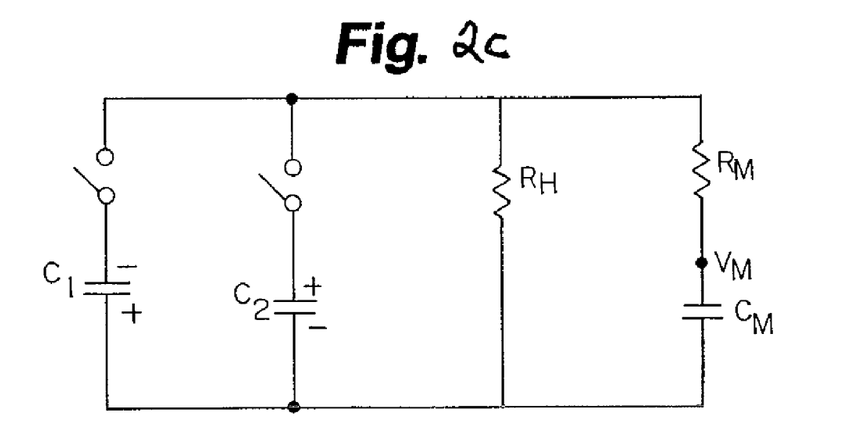
FIG. 2c depicts a basic defibrillation circuit for generating a biphasic waveform.

In a simplest form, a defibrillation circuit for AED 100 can be depicted as shown in FIG. 2*a* where $C_1$ represents a capacitor, $V_S$ represents the voltage between the electrodes $R_H$ represents the resistance of the heart. Further variations on the defibrillation circuit for AED 100 are shown in FIG. 2*b* representing a monophasic waveform circuit, and FIG. 2*c* depicting a biphasic waveform circuit. Within FIGS. 2*b* and 2*c*, $C_M$ and $R_M$ represent membrane series capacitance and resistance of a single cell, $V_M$ represents the voltage across the cell membrane and $C_1$ and $C_2$ refer to a first and second capacitors, or capacitor banks, respectively. In its simplest form, electrodes 114 communicate patient specific parameters to the AED 100 such that the patient resistance can be determined. Based on this resistance, the AED 100 discharges the capacitors to generate and deliver the shocking waveform, in either a monophasic or biphasic form. For more detail with respect to determining patient resistance and optimizing a shocking waveform, reference is made to Applicant's issued U.S. Pat. No. 6,411,846, which is commonly assigned to the assignee of the present invention and is hereby incorporated by reference in its entirety.

With respect to the present invention, the capacitors depicted within FIGS. 2*a*, 2*b* and 2*c* are variable capacitance capacitors. Generally, these variable capacitance capacitors each have a large positive voltage coefficient. The large positive voltage coefficient causes the capacitance of these variable capacitance capacitors to increase with a corresponding increase in the amount of charge being stored. A representative variable capacitance capacitor is the Pulse Power line of multilayer ceramic chip capacitors manufactured by Novacap.

The use of variable capacitance capacitors within the defibrillation circuits of FIGS. 2*a*, 2*b* and 2*c* has two significant advantages over the fixed capacitance capacitors presently used in defibrillation circuits. First, by storing energy at a lower voltage, the defibrillation circuit can deliver an initial defibrillation current at a current level lower than prior art designs such that the risk of tissue damage from said current is reduced. Secondly, the level of the defibrillation current is maintained avoiding the exponential decay in current level experienced by prior art designs.

With respect to the discharge characteristics of the variable capacitance capacitors, the characteristics are represented by the equation:

$$V=Q/C \qquad \text{Eq. 1}$$

where V is the capacitor voltage, Q is the charge amount and C is the capacitance. From this equation, it will be obvious that as capacitance decreases with the charge amount, the capacitor voltage is "lifted" such that it is prevented from decaying at an exponential rate. As the capacitor voltage is related to the defibrillation current by the equation:

$$V=I*Z \qquad \text{Eq. 2}$$

where V is the capacitor voltage, I is the defibrillation current and Z is the patient impedance, the defibrillation current follows the same behavior as the capacitor voltage, i.e., it is "lifted" such that it is prevented from decaying at an exponential rate, since the patient impedance remains essentially constant throughout the defibrillation discharge.

Figure 3:
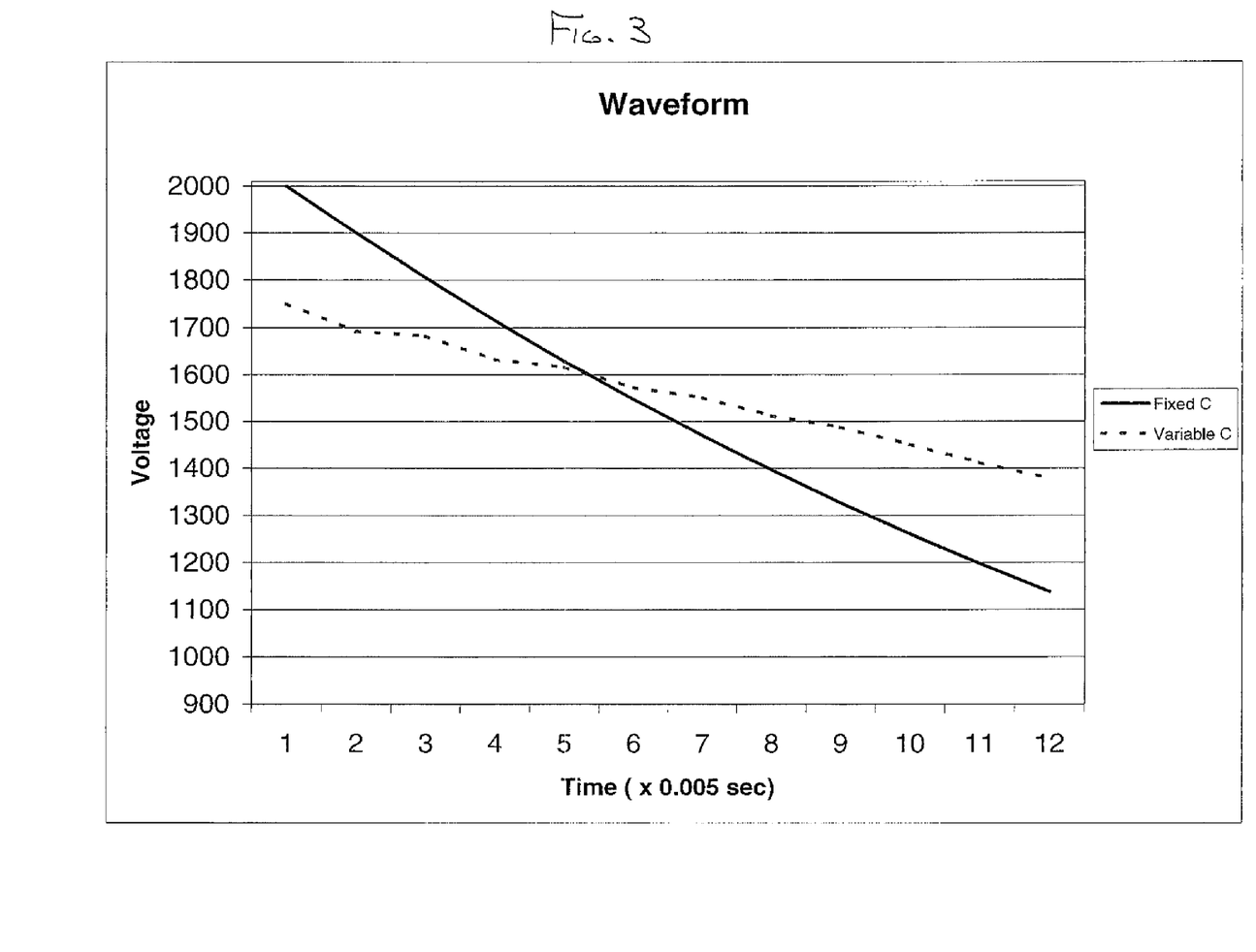
FIG. 3 depicts a comparison of Voltage versus Time for a defibrillator comprising a traditional fixed capacity capacitor and a defibrillator comprising a variable capacitance capacitor.
Figure 4:
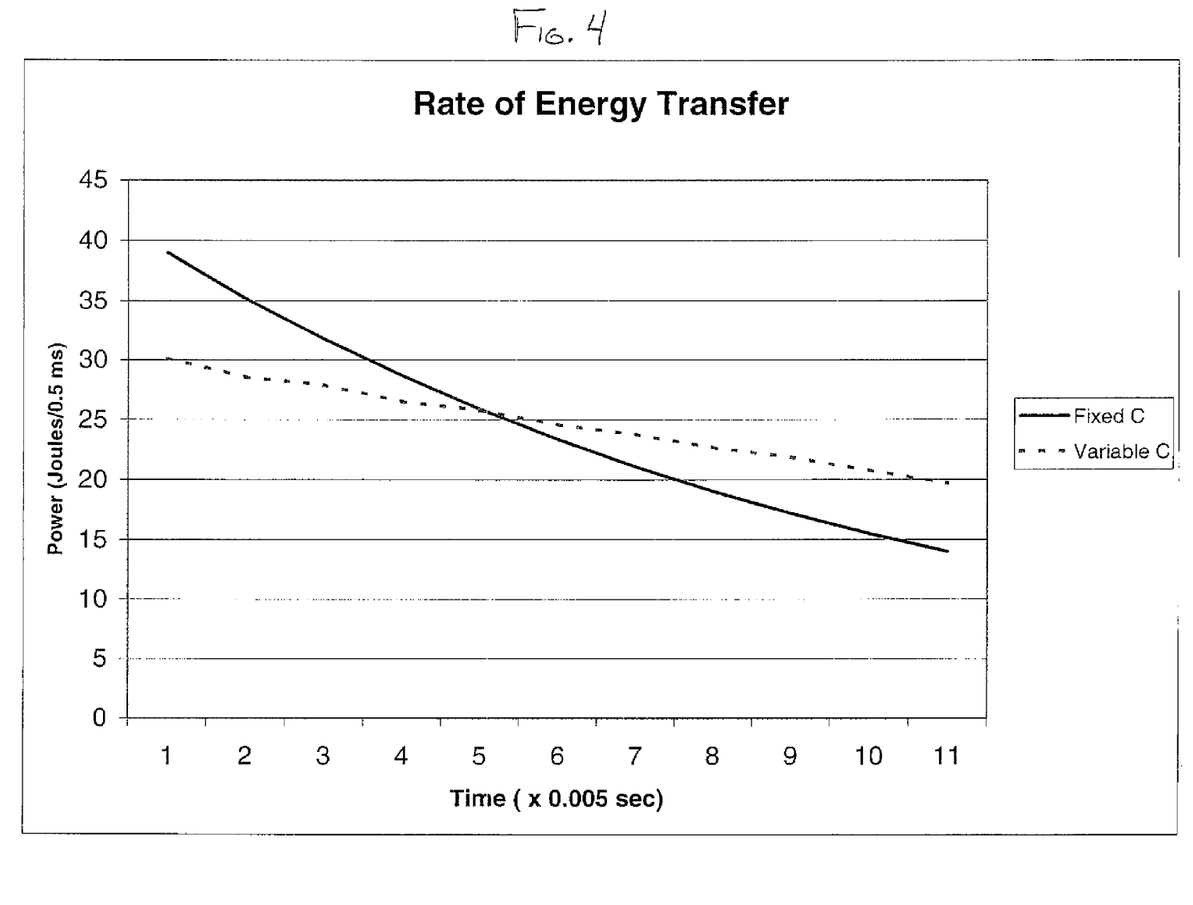
FIG. 4 depicts a comparison of Power versus Time for a defibrillator comprising a traditional fixed capacity capacitor and a defibrillator comprising a variable capacitance capacitor.

In practice, the benefits of the present invention are easily observable by comparing the defibrillation characteristics of a biphasic waveform generated using a traditional fixed capacitor rated for 200 uF at O volts with a biphasic waveform generated using a variable capacitance capacitor rated at 100 uF. For purposes of comparison, the patient impedance is assumed constant, i.e., 50. Using the aforementioned equations, data is generated for both traditional fixed capacitors as well as variable capacitance capacitors. Using this data, a graph of voltage versus time is illustrated in FIG. 3, while a graph of Power versus Time is illustrated in FIG. 4 to demonstrate the rate of energy transfer. The data used to generate FIGS. 3 and 4 is:

| Time (ms) | Voltage (V) Fixed Capacitor | Delivery Rate (J/ms) Fixed Capacitor | Voltage (V) Variable Capacitor | Delivery Rate (J/ms) Variable Capacitor |
| --- | --- | --- | --- | --- |
| 0 | 2000 |  | 1750 |  |
| .5 | 1900 | 39.0 | 1692 | 30.1 |
| .10 | 1805 | 35.2 | 1683 | 28.5 |
| .15 | 1715 | 31.8 | 1633 | 27.9 |
| .20 | 1629 | 28.7 | 1617 | 26.5 |
| .25 | 1548 | 25.9 | 1573 | 25.8 |
| .30 | 1470 | 23.4 | 1552 | 24.6 |
| .35 | 1397 | 21.1 | 1512 | 23.8 |
| .40 | 1327 | 19.0 | 1488 | 22.7 |
| .45 | 1260 | 17.2 | 1451 | 21.9 |
| .50 | 1197 | 15.5 | 1412 | 20.8 |
| .55 | 1138 | 14.0 | 1378 | 19.7 |

As illustrated by the graph of FIG. 3, the biphasic waveform using the traditional fixed capacitor is storing 2000 V as compared to the approximately 1750 V stored by the variable capacitance capacitor. Based on the aforementioned equations, generation of a biphasic waveform using the traditional fixed capacitor will have a higher initial current potentially causing tissue damage as compared to the variable capacitance capacitor. Furthermore, the characteristics of the variable capacitance capacitor will result in a greatly reduced voltage decay as time proceeds such that the effective defibrillation current can be maintained for a longer period. In comparison, the traditional fixed capacitor must have a high initial voltage to insure that it maintains an effective defibrillation current level throughout the exponential decay in voltage over time. Along these same lines, FIG. 4 illustrates that the use of a variable capacitance capacitor allows energy to be transferred through the biphasic waveform starting at a lower initial rate and maintaining the rate for a longer period in comparison to waveforms generated using traditional fixed capacitors.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

What is claimed:

1. A defibrillation apparatus, wherein said defibrillation apparatus delivers a shocking waveform to produce a desired cardiac response in the cardiac cell membrane of a patient, the apparatus comprising:
   a pair of electrodes, wherein said pair of electrodes are securable to said patient; and
   an electronic circuit, wherein said electronic circuit is operably coupled to said pair of electrodes, wherein said electronic circuit includes an energy storage portion that comprises at least one variable capacitance capacitor having a large positive voltage coefficient and a capacitance that significantly increases with an amount of charge contained by the variable capacitance capacitor and wherein said electronic circuit initiates delivery of said shocking waveform through said pair of electrodes upon detection of a shockable condition within said cardiac cell membrane.

2. The defibrillation apparatus of claim 1, wherein the defibrillation apparatus is an Automated External Defibrillator.

3. The defibrillation apparatus of claim 1, wherein the shocking waveform is a biphasic waveform.

4. The defibrillation apparatus of claim 1, wherein the electronic circuit further comprises an energy source wherein said energy source is a detachable battery pack.

5. The defibrillation apparatus of claim 1, wherein the energy storage portion comprises a plurality of variable capacitance capacitors arranged in either a parallel or series orientation.

6. The defibrillation apparatus of claim 5, wherein the plurality of variable capacitance capacitors define at least two charging banks within the energy storage portion.

7. The defibrillation apparatus of claim 1 wherein the energy storage portion further comprises at least one fixed capacitance capacitor.

8. A method for generating a shocking waveform for application to a cardiac cell membrane of a patient, the method comprising the steps of:
sensing at least one patient specific parameter to determine if defibrillation of said cardiac cell membrane is required;
charging an energy storage portion, wherein said energy storage portion comprises at least one variable capacitance capacitor having a large positive voltage coefficient and a capacitance that significantly increases with an amount of charge contained by the variable capacitance capacitor; and
discharging the energy storage portion in the form of a defibrillation waveform; and
delivering said defibrillation waveform to said cardiac cell membrane of said patient.

9. The method of claim 8, wherein the pair of electrodes are removably attachable to the patient.

10. The method of claim 8, wherein the shocking waveform is a biphasic waveform.

11. The method of claim 8, wherein the charging step further comprises charging a plurality of variable capacitance capacitors with an energy source, the plurality of variable capacitance capacitors arranged in either a series or parallel orientation.

12. The method of claim 11, wherein the plurality of variable capacitance capacitors define at least two distinct charging banks.

13. The method of claim 11, wherein the energy source is a detachable battery pack.

14. The method of claim 8, wherein the charging step further comprises charging at least one fixed capacitance capacitor.

15. A method of sustaining a level of defibrillation current during the delivery of a defibrillation waveform to the cardiac cell membrane of a patient, the method comprising the steps of:
sensing at least one patient specific parameter to determine if defibrillation of said cardiac cell membrane is required;
charging an energy storage portion, wherein said energy storage portion comprises at least one variable capacitance capacitor having a large positive voltage coefficient and a capacitance that significantly increases with an amount of charge contained by the variable capacitance capacitor; and
discharging the energy storage portion in the form of a defibrillation waveform, wherein upon discharging the energy storage portion a level of a defibrillation current of said energy source decays at a substantially linear rate; and
delivering said defibrillation waveform to said cardiac cell membrane of said patient.

16. A method of sustaining a level of defibrillation current during the delivery of a defibrillation waveform to the cardiac cell membrane of a patient, the method comprising the steps of:
sensing at least one patient specific parameter to determine if defibrillation of said cardiac cell membrane is required;
charging an energy storage portion, wherein said energy storage portion comprises at least one variable capacitance capacitor having a large positive voltage coefficient and a capacitance that significantly increases with an amount of charge contained by the variable capacitance capacitor; and
discharging the energy storage portion in the form of a defibrillation waveform, wherein said at least one variable capacitance capacitor has an initial defibrillation current and wherein said initial defibrillation current is less than the initial defibrillation current of a comparable non-variable capacitor that is capable of replacing said variable capacitance capacitor within said energy storage portion; and
delivering said defibrillation waveform to said cardiac cell membrane of said patient.

17. A method of sustaining a level of defibrillation current during the delivery of a defibrillation waveform to the cardiac cell membrane of a patient, comprising:
providing a defibrillation apparatus wherein said defibrillation apparatus delivers a shocking waveform to produce a desired cardiac response in the cardiac cell membrane of a patient;
providing instructions for sustaining defibrillation current, the instructions including:
sensing at least one patient specific parameter to determine if defibrillation of said cardiac cell membrane is required;
charging an energy storage portion, wherein said energy storage portion comprises at least one variable capacitance capacitor having a large positive voltage coefficient and a capacitance that significantly increases with an amount of charge contained by the variable capacitance capacitor;
discharging the energy storage portion in the form of a defibrillation waveform, wherein upon discharging the energy storage portion a level of a defibrillation current of said energy source decays at a substantially linear rate; and
delivering said defibrillation waveform to said cardiac cell membrane of said patient.

18. A method of sustaining a level of defibrillation current during the delivery of a defibrillation waveform to the cardiac cell membrane of a patient, comprising:
- providing a defibrillation apparatus wherein said defibrillation apparatus delivers a shocking waveform to produce a desired cardiac response in the cardiac cell membrane of a patient;
- providing instructions for sustaining defibrillation current, the instructions including:
  - sensing at least one patient specific parameter to determine if defibrillation of said cardiac cell membrane is required;
  - charging an energy storage portion, wherein said energy storage portion comprises at least one variable capacitance capacitor having a large positive voltage coefficient and a capacitance that significantly increases with an amount of charge contained by the variable capacitance capacitor;
  - discharging the energy storage portion in the form of a defibrillation waveform, wherein said at least one variable capacitance capacitor has an initial defibrillation current and wherein said initial defibrillation current is less than the initial defibrillation current of a comparable non-variable capacitor that is capable of replacing said variable capacitance capacitor within said energy storage portion; and
  - delivering said defibrillation waveform to said cardiac cell membrane of said patient.

* * * * *